(12) United States Patent
Merrill et al.

(10) Patent No.: US 9,458,569 B2
(45) Date of Patent: Oct. 4, 2016

(54) WET OXIDATION OF BIOMASS

(71) Applicant: CLEAN-VANTAGE LLC, Richland, WA (US)

(72) Inventors: Richard Alan Merrill, Richland, WA (US); Kenn Petersen, Richland, WA (US)

(73) Assignee: CLEAN-VANTAGE LLC, Richland, WA (US)

( * ) Notice: Subject to any disclaimer, the term of this patent is extended or adjusted under 35 U.S.C. 154(b) by 2 days.

(21) Appl. No.: 14/157,518

(22) Filed: Jan. 16, 2014

(65) Prior Publication Data

US 2014/0199740 A1 Jul. 17, 2014

Related U.S. Application Data

(60) Provisional application No. 61/753,098, filed on Jan. 16, 2013.

(51) Int. Cl.
| | |
|---|---|
| C12P 7/64 | (2006.01) |
| D21C 1/02 | (2006.01) |
| D21C 1/08 | (2006.01) |
| C08H 7/00 | (2011.01) |
| C08H 8/00 | (2010.01) |
| D21C 3/04 | (2006.01) |
| D21C 11/00 | (2006.01) |

(52) U.S. Cl.
CPC ........ D21C 1/02 (2013.01); C08H 6/00 (2013.01); C08H 8/00 (2013.01); D21C 1/08 (2013.01); D21C 3/045 (2013.01); D21C 11/0007 (2013.01); *C12P 2201/00* (2013.01); *C12P 2203/00* (2013.01)

(58) Field of Classification Search
None
See application file for complete search history.

(56) References Cited

U.S. PATENT DOCUMENTS

| 4,229,296 A | 10/1980 | Wheaton et al. |
| 2007/0148751 A1 | 6/2007 | Griffin et al. |
| 2009/0117635 A1* | 5/2009 | Bradley et al. ............... 435/165 |
| 2009/0178671 A1 | 7/2009 | Munck |

FOREIGN PATENT DOCUMENTS

| EP | 2520608 A1 | 11/2012 |
| WO | 2004108609 A1 | 12/2004 |

OTHER PUBLICATIONS

Petersen, et al. "Optimization of hydrothermal pretreatment of wheat straw for production of bioethanol at low water consumption without addition of chemicals", Biomass and Bioenergy 2009, vol. 33, pp. 834-840.*
International Search Report and Written Opinion of the International Searching Authority, issued Apr. 15, 2014 in International Application No. PCT/US2014/011944.

* cited by examiner

*Primary Examiner* — Michelle F Paguio Frising
(74) *Attorney, Agent, or Firm* — Jeffrey Parry Intellectual Property Law Group PLLC; Jeffrey C. Parry

(57) ABSTRACT

The present disclosure comprises methods, apparatus, components, and techniques for pretreatment of biomaterials using targeted wet oxidation. The targeted wet oxidation pretreatment is an upstream method for converting solid biomass into fuels and/or specialty chemicals. Embodiments of the present disclosure comprise methods carried out on biomaterials to selectively oxidize lignin components of the biomass, thereby resulting in bio accessible/digestible biomass fibers. In embodiments of the present disclosure, such methods may comprise pretreatment processes to prepare the biomaterials for a subsequent fermentation or other like conversion may be carried out to result in useful bio fuels or other bioproducts.

16 Claims, No Drawings

WET OXIDATION OF BIOMASS

CROSS-REFERENCE TO RELATED APPLICATIONS

This application claims priority under 35 USC §119 to U.S. Provisional Patent Application Ser. No. 61/753,098, filed Jan. 16, 2013, and titled "METHOD AND EQUIPMENT FOR PROCESSING LIGNOCELLULOSIC BIOMASS AT HIGH DRY MATTER CONTENT BY TARGETED WET OXIDATION WITHOUT CO2 ACCUMULATION RESULTING IN HIGHER PRETREATMENT pH AND LOWER INHIBITOR CONCENTRATION," the entire contents of which are hereby incorporated by reference.

BACKGROUND

1. Technical Field

The present disclosure relates generally to pretreatment of biomass using oxygen. In particular, the present disclosure relates to wet combustion of lignin components in a preconditioned biomass.

2. Description of Related Art

General definitions of "biomass" or "biomaterials" may include agricultural commodities and residues, plants and trees, algae, crop residues, waste material (including wood waste and wood residues), animal waste and byproducts (including fats, oils, greases, and manure), construction waste, and food and yard waste. Readily available sources of biomass may include agricultural crop residues (e.g., straw, corn stover, bagasse, husk, and hull etc.), purpose grown energy crops (e.g., Miscanthus and switch grass), forest residues (e.g., saw mill residues, wood chips, forest thinnings, hog fuel, and scrap wood), and wastes (e.g., municipal solid waste ("MSW") including green waste, industrial food processing waste, manure, and sewage sludge ("SS")).

These biomass materials may be produced in great abundance, but much of such materials may lack commercially viable end uses. In the cases of MSW and SS, great expenditures of public funds are typically used to dispose of such wastes, including costs involved in the collection, treatment, transport, and final disposal. The recovery of energy (i.e., fuels) or chemical products from biomass could avoid the costs of disposal as well as reduce reliance on non-renewable fossil fuel resources which commonly serve as feedstock for the production of many industrial chemicals.

However, many such biomass materials may contain lignin, hemicellulose, cellulose, and/or other like constituent components in varying amounts. Such biomass components may reduce the bioaccessibility of the biomass and be inhibitory for production of desirable fuels and other bioproducts from the biomass.

DETAILED DESCRIPTION

In the following description, reference is made to exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the spirit and scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

Embodiments of the present disclosure provide methods, apparatus, components, and/or techniques for biomaterial pretreatment using targeted wet oxidation. In a targeted wet oxidation pretreatment operation, the bioaccessibility of biomass components can be enhanced. Embodiments of the present disclosure comprise methods performed on biomaterials to selectively oxidize lignin components of the biomass, thereby resulting in bioaccessible/digestible biomass fibers. In embodiments of the present disclosure, such methods may comprise pretreatment processes carried out to prepare the biomaterials for a subsequent fermentation or other like conversion, which may result in the production of useful biofuels or other bioproducts.

According to embodiments, biomass feedstocks can be pretreated using water, heat, and moderated concentrations of oxygen to open up the lignocellulosic structure of the biomaterials. Embodiments of the present disclosure comprise semi-continuous or continuous processes carried out in one or more reaction vessels. In general, such processes pretreat biomass at relatively high dry biomass matter content and at a controlled oxygen partial pressure. Such processes may be referred to herein as a "targeted wet oxidation" processes. A product of such processes comprises a slurry that may be referred to herein as a "pretreated slurry." The pretreated slurry from the targeted wet oxidation processes of the present disclosure can subsequently be hydrolyzed using enzymes to produce a sugar stream or may, fermented using a biochemical process to produce useful compounds such as volatile fatty acids ("VFAs"), alcohols, ketones, methane, and other hydrocarbons.

According to embodiments of the present disclosure, a targeted wet oxidation process can be carried out in an integrated system that first preconditions the biomass in a semi-continuous system followed by application of a pretreatment operation. Embodiments of the present disclosure comprise a reaction assembly for carrying out the various processes disclosed herein. Embodiments of the reaction assembly comprise a feed hopper, a screw press, a feed sluice that is fed from the feed hopper, a pretreatment reactor, and a flash tank.

In embodiments, preconditioned biomass may be collected in the feed hopper. Embodiments of the feed hopper comprises a high speed feed screw. A feed sluice inlet valve that is disposed between the feed hopper and the feed sluice may selectively allow fluid communication between the feed hopper and the feed sluice, so that biomass can pass from the feed hopper into the feed sluice while the feed sluice valve is open. In embodiments, the feed sluice comprises a pressure vessel. Embodiments of the feed sluice comprise a high pressure steam inlet, a recycled steam inlet, and a feed sluice vent valve. In some embodiments, the feed sluice further comprises a vent line to let down the pressure in the sluice before opening the inlet valve. In embodiments, each steam inlet conduit comprises a valve. Embodiments of the feed sluice further comprise a feed sluice outlet valve and feed sluice outlet conduit that leads to the pretreatment reactor.

While the feed sluice outlet valve is open, biomass can pass from the feed sluice into the pretreatment reactor via a sluiced feed system. In embodiments, the feed sluice and pretreatment reactor comprise pressure reaction vessels. In particular, embodiments of the feed sluice and/or pretreatment reactor can withstand internal pressures of up to 47 bar(g).

In embodiments, the feed sluice is smaller in volume than the pretreatment reactor. For example, embodiments of the feed sluice comprise a volume that is 1-50% of the pretreatment reactor volume.

Embodiments of the pretreatment reactor comprise an inlet conduit from the feed sluice, a pressure relief valve, a venting conduit with a venting valve, an outlet conduit leading to the flash tank, and one or more steam inlets. In embodiments, the venting conduit and venting valve are at or near the top of the pretreatment reactor. In embodiments, the pretreatment reactor has one or more introduction zones. An introduction zone comprises a zone wherein oxygen and steam are fed into the pretreatment reactor. In embodiments, an introduction zone comprises a ring circumscribing an interior volume of the pretreatment reactor. The ring comprises numerous inward-facing introduction ports, through which high pressure steam, oxygen, or a mixture of both can be fed into the pretreatment reactor. In one embodiment, the pretreatment reactor comprises three flanges, each flange representing an introduction zone. Each introduction zone may be fed by an inlet conduit having a valve. Additional or fewer introduction zones can be applied depending on the biomass being pretreated and other process considerations. A pretreatment reactor is made of a series of connected segments that jointly comprise a tube-type reactor.

Embodiments of a vertical pretreatment reactor have a height-to-diameter ratio of, as an example, 12 to 2. Alternative embodiments comprise a pretreatment reactor comprising a horizontal reaction vessel having a length-to-diameter ratio of, as an example, 12 to 2. Alternative embodiments having different dimensions, numbers of introduction zones, and/or size ratios may also carry out the processes of the present disclosure. Embodiments of the pretreatment reactor can have a number of introduction zones, ranging from 0.000001 to 10 zones per liter of reactor volume.

In embodiments, the pretreatment reactor is equipped with a mixer. The mixer is configured in a way that effectuates consistent mixing within the pretreatment reactor, thereby preventing or mitigating biomass buildup. One purpose of the mixer may be to keep the pretreatment reactor sidewalls clear of biomass buildup and to mitigate gas pocket formation in the biomass slurry. Mixing may allow for the gas to reach the venting conduit and valve, where it is continuously or semi-continuously vented from the pretreatment reactor. Additionally, mixing may help to move the biomass slurry through the reactor and promote uniformity of process conditions.

The outlet conduit leads from the pretreatment reactor to the flash tank. In embodiments, the outlet conduit has a valve installed thereon to regulate the flow of biomass slurry into the flash tank. The flash tank receives pretreated biomass from the pretreatment reactor. In embodiments, the flash tank is equipped with a return loop to the recycled steam inlet valve of the feed sluice, thereby enabling part of the steam in the flash tank to be recycled back to the feed sluice.

In embodiments, the flash tank is equipped with a mixer to help move the pretreated slurry through the flash tank to downstream processing. Embodiments of the flash tank comprise a volume between 1% and 90% of the pretreatment reactor volume.

In operation, biomass is pretreated using a targeted wet oxidation process carried out in one or more reactor systems including a feed sluice, pretreatment reactor, and flash tank, resulting in the pretreated slurry. The biomass may be fed into a semi-continuous or continuous type reaction vessel via a high-pressure sluiced inlet chamber. In some embodiments, biomass is preconditioned as described below prior to feeding into the reactor. In general, oxygen and steam may be added to the biomass in the pretreatment reactor to effect the pretreatment process. After the pretreatment reactions are carried out, the pretreated slurry can be flashed from the reactor into the flash tank.

Examples of biomass feedstock that could be processed in operations of the present disclosure include, but are not limited to: manure, corn stover, straw and other agricultural residues, wood, municipal household waste, and slaughter house waste. In general, pretreatment of biomass may be more effective if the biomass has been reduced in size. Biomass size reduction may be carried out by using commonly available size reduction equipment, such as a chipper, shredder, or grinder to yield a biomass no larger than approximately two inches in size. In alternative embodiments, other biomass feedstock sizes may be used.

Some embodiments of the present disclosure comprise operations where biomass is preconditioned prior to the wet oxidation pretreatment process. This preconditioning process may be carried out, for example, through extraction processes where salts and/or water soluble xylan, xylose, and/or cellulose are removed from the biomass. In general, preconditioning methods of the present disclosure may be carried out to precondition biomass to obtain a relatively high concentration of lignin components in biomass fibers. The preconditioning and/or extraction step may also allow water to penetrate deep into the biomass, thus creating an oxidizing dampener throughout the lignocellulosic structure. As a result of the preconditioning/extraction, the lignocellulosic structure may also become more porous, thus creating a larger surface area for the oxygen to react with. As a result, the lignin in the biomass may be more easily targeted for wet oxidation.

In embodiments, incoming biomass feedstock may be preconditioned in a soaking process, where the biomass is soaked in water at approximately 60° C. for a period of up to four hours to form an aqueous slurry. To enhance the removal of salts from certain types of biomass, the soaking temperature may be increased to 90° C. In alternative embodiments, dirt or a biomass feedstock may selectively be preconditioned by washing with water at approximately 20° C. In embodiments, the prepared biomass feedstock may then be transferred using a feedstock transfer pump and piping system for biomass preconditioning operations. In an alternative embodiment, the biomaterial could be dewatered and transferred as a bulk solid. Alternatively, the material could be converted to a slurry with or without washing.

The feedstock receiving, processing, and preparation operations may also include biological pre-processing using anaerobic digestion ("AD"). An AD operation may be carried out to convert some of the readily available biomass components like sugar monomers, oligomers, and organic acids from the feed stock into biogas before wet oxidation, which may be carried out on the solids left after AD. Removal of easily digestible biomass components, such as readily available sugar monomers, oligomers, and organic acids may reduce unwanted reactions that could otherwise happen if raw or untreated lignocellulosic biomass were subjected to wet oxidation. Undesirable reactions during wet oxidation could form compounds that can inhibit microbial activity in subsequent bioconversion processes.

In some embodiments, preconditioning a biomass comprises realizing a target dry matter content in the biomass. For example, the biomass can be preconditioned in a screw press to achieve a dry matter content (by weight) of 15-60%. As further examples, the biomass may be preconditioned to achieve a dry matter content of 20-50%, 25-55%, or 30-50%. In embodiments, heating by steam is carried out during the screw press operation.

In embodiments, preconditioned biomass may be fed into the feed hopper at selected pressures ranging from ambient to approximately 47 bars. At such operations, the feed sluice inlet valve remains open to allow passage of the biomass into the feed sluice from the feed hopper. While biomass is transferred into the feed sluice, the feed sluice outlet valve may be closed and the feed sluice vent valve may be open. After filling, the feed sluice inlet valve and the feed sluice vent valve can be closed. According to embodiments, the preconditioned biomass within the feed sluice can then be preheated using a combination of, for example, recycled steam at the recycled steam inlet and high pressure steam at the high pressure steam inlet. In one embodiment, the high pressure steam is at a temperature of between 110 and 260° C. at 0.42-46 bar(g). The recycled steam may comprise low pressure steam recovered via a return loop from the flash tank to the recycled steam inlet valve of the feed sluice. In embodiments, the feed sluice can be pressurized using high pressure steam to pressurize the biomass materials prior to feeding into the pretreatment reactor.

The feed sluice outlet valve can be flashed open at a temperature between 110-260° C. In embodiments, the feed sluice outlet valve is flashed open upon reaching a specific threshold for the volume of biomass within the feed sluice. Alternatively, in other embodiments, the feed sluice outlet valve is flashed open upon satisfaction of conditions relating to the volume of biomass within the feed sluice as it relates to a biomass inlet flow rate. For example, the feed sluice outlet valve can be flashed open upon a determination that in x minutes, the biomass would otherwise fill the feed sluice, where x may be any selected time value including, but not limited to, 0.001-60 minutes. According to embodiments, the feed sluice outlet valve may be open for 0.01-10 seconds. This action may result in a flash release of the feed sluice contents into the pretreatment reactor. The feed sluice outlet valve is then closed and the remaining pressure in the feed sluice is released through the feed sluice vent valve.

In example embodiments, the pretreatment reactor temperature is maintained at 150 to 230° C. at a pressure of 10 to 40 bars. In embodiments, the biomass temperature is manipulated via the introduction zones by selectively adjusting the temperature and/or amount of steam introduced, thereby forming a temperature gradient along the first part of the pretreatment reactor from 110° C. to the desired temperature such as 175 to 230° C.

The wet oxidation reaction is propagated within the pretreatment reactor by introducing steam and oxygen to the biomass at the elevated temperatures and pressures. The venting valve may be opened to vent carbon dioxide, carbon, monoxide, oxygen, and other exhaust gasses from the pretreatment reactor. A selective venting and/or introduction of steam/oxygen can allow for a controlled oxygen partial pressure within the pretreatment reactor. By controlling the oxygen partial pressure within the pretreatment reactor, the oxidation rate of the preconditioned biomass can also be controlled. Continuously adding oxygen to the pretreatment reactor and maintaining the pretreatment reactor pressure at a constant level by venting gases from the reactor as they are produced may cause the carbon dioxide and oxygen concentrations to be lower than in a batch type wet oxidation operation. In such a batch system, the reactor pressure is typically the sum of the steam pressure (at the reaction temperature) plus the partial pressure of the oxygen loading. By maintaining a substantially constant reaction pressure and temperature during the continuous oxygen dosage, and by continuously removing carbon dioxide, the continuous process can result in a relatively low carbon dioxide concentration and a relatively high oxygen dosage. Further, the continuous process may also prevent carbon dioxide from accumulating within the pretreatment reactor.

Accumulated carbon dioxide in the pretreatment reactor could dissolve into the water phase, resulting in a drop in pH. Venting the carbon dioxide may thus control the pH at a higher, desirable level and thereby reduce the number of undesirable acid-catalyzed reactions occurring during the oxidation process. These acid-catalyzed reactions are known to form compounds that can inhibit further downstream processing, included but not limited to biological downstream processing.

In embodiments, during the pretreatment phase, the amount of available oxygen is in the range of 0.01 to 15% of chemical oxygen demand ("COD"). In other embodiments, the amount of added oxygen is between 0.1 to 10% of COD.

In embodiments, biomass is retained within the pretreatment vessel and subjected to steam and oxygen introduction for 1 to 60 minutes. In other embodiments, the biomass is retained in the pretreatment vessel for 5 to 30 minutes.

In embodiments of the present disclosure, the steam is added with the oxygen, therefore causing wet oxidation to occur as soon as the temperature reaches a critical temperature for a specific biomass compound to be oxidized. In these embodiments, the wet oxidation reaction can begin as the temperature approaches a target temperature for that reaction. In other processes, the temperature and pressure may increase beyond the target temperature while and after the oxygen is added.

In methods of the present disclosure, the differences in solubility (in water) of the oxygen introduced into the pretreatment reactor and the solubility (in water) of reaction products such as carbon monoxide and carbon dioxide can enable partial gas separation. Partial gas separation may allow for a better integration of process streams and an overall improved process economy. For example, inside the reactor, the gas phase may contain more oxygen than the liquid phase, while the liquid phase contains more carbon dioxide than the gas phase.

In some embodiments of the present disclosure, oxygen, acid, and/or oxygen combined with acid or base are further added to the biomass in a pretreatment process to make the biomass structure more accessible for biological degradation. Examples of acids that may be added include sulfuric acid at concentrations from 0.001 to10%, phosphoric acid or hydro chloric acid at concentrations from 0.001 to10%, or acetic acids at concentrations from 0.1 to 25%. Examples of bases that may be added include sodium hydroxide or potassium hydroxide, sodium carbonate or calcium carbonate at concentrations from 0.1 to 20%.

After biomass is introduced into the pretreatment reactor, the biomass may travel through the pretreatment reactor in a plug flow. The biomass can be flashed out through the outlet conduit leading to the flash tank as pretreated biomass.

Steam in the flash tank can be recycled back through the system via the return loop from the flash tank to the recycled steam inlet valve of the feed sluice. Remaining steam pressure can transport the pretreated slurry downstream from the flash tank. The process may then begin again with new preconditioned biomaterial entering the feed sluice.

As will be understood by those of ordinary skill in the art having the benefit of this disclosure, embodiments and methods set forth herein may present several advantages over other methods of pretreating biomaterials. For example, embodiments of the present disclosure comprise a continuous process. Accordingly, the pretreatment reactor may not undergo significant temperature and pressure fluctuations, as may be associated with a batch type operation.

Additionally, due to the high dry matter content of the preconditioned biomass, processes of the present disclosure may consume less energy to heat the reaction mixture and may have less demanding equipment needs, thus reducing operational costs. As another benefit of some embodiments, relatively low carbon dioxide concentrations relative to traditional methods and no acid addition may result in less corrosive pretreatment conditions due to higher pH, thus prolonging the lifespan of equipment and apparatus employed to carry out the processes.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the spirit and scope of the present disclosure.

What is claimed is:

1. A method of pretreating a biomass slurry in a continuous process, comprising:
   in the continuous process, obtaining a dry matter content of the biomass slurry of 15-60% by weight;
   in the continuous process, introducing a flow of steam to a reaction chamber containing the biomass slurry;
   while introducing the flow of steam to the reaction chamber, introducing a flow of oxygen to the reaction chamber and the biomass slurry, thereby causing oxidation of a lignin component of the biomass slurry; and
   in the continuous process, flashing the biomass to a secondary holding unit by utilizing a pressure difference.

2. The method of claim 1, wherein obtaining a dry matter content of the biomass slurry of between 15-60% further comprises feeding the biomass slurry into a screw press.

3. The method of claim 1, wherein obtaining a dry matter content of the biomass slurry of 15-60% by weight further comprises introducing steam into the biomass slurry.

4. The method of claim 1, wherein obtaining a dry matter content of the biomass slurry of 15-60% by weight further comprises obtaining a dry matter content of 25-55% by weight.

5. The method of claim 1, wherein obtaining a dry matter content of the biomass slurry of 15-60% by weight further comprises obtaining a dry matter content of 30-50% by weight.

6. The method of claim 1, further comprising: in the continuous process, preconditioning the biomass slurry by extracting a nontargeted substance from the biomass slurry.

7. The method of claim 6, wherein the nontargeted substance comprises xylan.

8. The method of claim 6, wherein preconditioning the biomass slurry comprises soaking the biomass with water having a temperature between 60 and 90 degrees Celsius.

9. The method of claim 1, further comprising an anaerobic digestion pre-processing operation.

10. The method of claim 1, wherein following oxidation of the lignin component of the biomass slurry, the biomass slurry is subjected to a fermentation operation.

11. The method of claim 1, further comprising venting carbon dioxide from the reaction chamber to maintain the amount of available oxygen within the reaction chamber at 0.01-15% of chemical oxygen demand.

12. The method of claim 11, wherein venting carbon dioxide from the reaction chamber to maintain the amount of added oxygen within the reaction chamber at 0.01 to 15% of chemical oxygen demand further comprises venting carbon dioxide from the reaction chamber to maintain the amount of added oxygen within the reaction chamber at 0.1 to 10% of chemical oxygen demand.

13. A method of oxidizing lignin components in a biomass slurry, comprising:
   in a continuous process, removing water from the biomass slurry to achieve a dry matter content of 15-60% by weight;
   in the continuous process, concurrently subjecting the biomass slurry to a stream of oxygen and a stream of steam; and
   in the continuous process, flashing the biomass to a secondary holding unit by utilizing a pressure difference.

14. The method of claim 13, wherein the stream of steam is at a temperature of 110 to 260 degrees Celsius.

15. The method of claim 13, wherein removing water from the biomass slurry to achieve a dry matter content of 15-60% by weight comprises passing the biomass slurry through a screw press.

16. The method of claim 13, further comprising venting carbon dioxide from the biomass slurry.

* * * * *